(12) United States Patent
Hyvonen et al.

(10) Patent No.: US 12,119,102 B1
(45) Date of Patent: Oct. 15, 2024

(54) MACHINE-LEARNING MODELING TO GENERATE VIRTUAL BOLUS ATTRIBUTES

(71) Applicant: SIEMENS HEALTHINEERS INTERNATIONAL AG, Steinhausen (CH)

(72) Inventors: Heini Hyvonen, Helsinki (FI); Hannu Laaksonen, Espoo (FI); Ville Pietila, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 392 days.

(21) Appl. No.: 17/530,383

(22) Filed: Nov. 18, 2021

(51) Int. Cl.
*G16H 30/40* (2018.01)
*A61N 5/10* (2006.01)
*G06T 7/00* (2017.01)
*G16H 50/20* (2018.01)

(52) U.S. Cl.
CPC .......... *G16H 30/40* (2018.01); *A61N 5/1064* (2013.01); *G06T 7/0012* (2013.01); *G16H 50/20* (2018.01); *A61N 2005/1074* (2013.01); *G06T 2200/24* (2013.01); *G06T 2207/20081* (2013.01); *G06T 2207/30004* (2013.01)

(58) Field of Classification Search
None
See application file for complete search history.

(56) References Cited

U.S. PATENT DOCUMENTS

| | | |
|---|---|---|
| 2019/0030371 A1 | 1/2019 | Han |
| 2019/0192880 A1 | 6/2019 | Hibbard |
| 2019/0333623 A1 | 10/2019 | Hibbard |
| 2021/0192719 A1 | 6/2021 | Laaksonen et al. |
| 2021/0299471 A1 | 9/2021 | Yang et al. |
| 2023/0293907 A1* | 9/2023 | Shade .................. A61N 5/1031 600/1 |

* cited by examiner

*Primary Examiner* — Leon Flores
(74) *Attorney, Agent, or Firm* — FOLEY & LARDNER LLP (57) ABSTRACT

Disclosed herein are methods and systems for predicting a virtual bolus in order to generate a radiation therapy treatment plan comprising training, by a processor, a machine-learning model using a training dataset comprising a set of medical images corresponding to a set of previously performed radiation therapy treatments, each medical image comprising at least one planning target volume and a non-anatomical region added to the medical image; and executing, by the processor, the machine-learning model using a medical image not included within the training dataset, the machine-learning model predicting an attribute of a non-anatomical region for the medical image not included in the training dataset.

20 Claims, 5 Drawing Sheets

MACHINE-LEARNING MODELING TO GENERATE VIRTUAL BOLUS ATTRIBUTES

TECHNICAL FIELD

This application relates generally to using machine-learning modeling to suggest radiotherapy treatment attributes in radiation therapy treatment procedures and specifically to predicting virtual bolus attributes.

BACKGROUND

Radiotherapy (radiation-based therapy) is used as a cancer treatment by emitting high doses of radiation that can kill cells or shrink a tumor. The target region of a patient's anatomy that is intended to receive radiation (e.g., tumor) is referred to as the planning target volume (PTV). Due to the extreme nature of the radiation emitted from the radiation therapy machine, a treatment plan must be precisely calculated and followed. The goal of the treatment plan is to allow the radiotherapy machine to deliver enough radiation to the PTV to kill the cancerous cells. However, this goal must be balanced against the risk of damaging or harming other cells that belong to other organs or anatomical regions that are adjacent to, or surrounding, the PTV. These organs or anatomical regions are referred to as organs at risk (OARs).

A treatment plan may identify various attributes of a radiotherapy machine configured for the patient's treatment, such as intensity-modulated radiation therapy (IM RT) parameters (e.g., the number of radiation beams and the beam angles (radiation delivery directions)), volumetric modulated arc therapy (VMAT) parameters (e.g., number and extent of arcs (full or partial)), multi-leaf collimator (MLC) opening, collimator angles, collimator jaw positions, avoidance sectors, isocenter positioning strategy, couch rotation, couch angles and the like.

In radiation therapy planning, the actual tumor site (Gross Tumor Volume (GTV)) and its clinical extension (Clinical Target Volume or CTV) are extended to a structure referred to as the PTV. This extension accounts for inaccuracies and uncertainties during the treatment delivery process, such as, but not limited to, the patient moving or breathing. Commonly the PTV encompasses an area larger than the CTV. In the treatment of certain disease sites, such as but not limited to breast treatments, breathing movement can cause the PTV to move beyond the actual body surface into air.

This movement of the PTV beyond the patient's body surface (e.g., into the air) creates a problem when planning and implementing the patient's treatment. Under today's standard treatment planning processes the planning optimizer will create MLC leaf openings (apertures) that do not in fact cover the entire PTV, as fields perpendicular to the patient surface will be assigned as zero dose outside the patient's surface. To correct this issue, conventional methods require a medical professional to create a virtual bolus with PTV and body extensions to be used during the treatment planning. For clarity, in breast treatments, real (e.g., physical) boluses are typically used to get the desired dose distribution when the patient's tumor is very superficial, however, these physical boluses are generally not used to account for the patient's breathing motion. The virtual bolus, as used herein, may represent an extension of the PTV outside of the body that is created for the plan optimization purposes (e.g., to be ingested by a plan optimization algorithm or a computer model that generates the MLC openings). The virtual bolus allows the optimization algorithm to automatically generate the planned MLC openings outside the body surface. Another conventional method requires the medical professional to modify the MLC opening or aperture, thereby extending the opening outside the original PTV.

Neither of the above-described conventional methods is desirable because both methods involve manual processes that are unreliable, time-consuming, and tedious (e.g., these conventional methods use inefficient trial and error processes). Because conventional methods heavily rely on the medical professional's subjective skills, these methods typically produce unreliable and inconsistent results.

SUMMARY

For the aforementioned reasons, there is a need to account for patients' movements during treatment in a manner that is automatic, efficient, and that produces reliable results. There is also a need to account for PTV extension recommendations that do not depend on subjective skills and understanding of medical professionals. Disclosed herein are systems and methods capable of offering continually refined recommendations for PTV adjustments. These adjustments can be ingested by a plan optimizer model to generate a treatment plan. Using the medical professional's prior decisions and previous treatments, a continuously trained machine-learning model may be used to predict one or more parameters needed to efficiently generate a PTV recommendation for a patient. For instance, the machine-learning model may predict a virtual bolus and transmit attributes of the virtual bolus to a downstream application.

The methods and systems described herein allow the machine-learning model to gradually adapt to new data distributions, making the machine-learning model less sensitive (more resistant) to data distribution changes. For example, in some implementations, a new solution(s) may be added. As a result, the machine-learning model may be able to accommodate new solution(s) and gradually adapt and customize its predictions.

The machine-learning model(s) discussed herein can learn to predict parameters needed by a plan optimizer model to generate a treatment plan depending on patient data as context. Patient data may include medical images (computed tomography (CT) images, cone-beam CT images (CBCT), four-dimensional CT images (e.g., CT images over time), magnetic resonance imaging (MRI) images, positron emission tomography (PET) images, ultrasound images, images obtained via some other imaging modality, or a combination thereof), patient information (e.g., height, weight, body mass index (BMI), diagnosis information (including anatomical attributes such as PTVs and/or OARs), age, equipment (e.g., pacemaker, respirator)), and the like.

In an embodiment, a method comprises executing, by a processor, a machine-learning model using a medical image not used to train the machine learning model to predict an attribute of a non-anatomical region for the medical image, wherein the machine-learning model has been trained using a set of medical images corresponding to a set of previously performed radiation therapy treatments, each medical image comprising at least one planning target volume and an added non-anatomical region for its respective radiation therapy treatment.

The non-anatomical region may correspond to material configured to reduce or increase radiation emitted towards the planning target volume.

The non-anatomical region may have an electron density value or a mass density value corresponding to human flesh.

The attribute of the non-anatomical region may correspond to a thickness of the non-anatomical region.

The attribute of the non-anatomical region may correspond to a position of the non-anatomical region in relation to the planning target volume.

The attribute of the non-anatomical region may correspond to a position of the non-anatomical region compared to an organ of the patient.

Each medical image within the set of medical images may comprise an indication of whether its corresponding non-anatomical region is acceptable.

The method may further comprise instructing, by the processor, a radiation therapy machine to adjust at least one of its attributes in accordance with the attribute of the non-anatomical region.

The method may further comprise transmitting, by the processor, the attribute of the non-anatomical region to a computing device to be displayed on a graphical user interface.

The method may further comprise transmitting, by the processor, a revised medical image that comprises the medical image not used to train the machine-learning model and a depiction of the non-anatomical region predicted by the machine-learning model.

In another embodiment, a system may comprise a server comprising a processor and a non-transitory computer-readable medium containing instructions that when executed by the processor causes the processor to perform operations comprising executing a machine-learning model using a medical image not used to train the machine learning model to predict an attribute of a non-anatomical region for the medical image, wherein the machine-learning model has been trained using a set of medical images corresponding to a set of previously performed radiation therapy treatments, each medical image comprising at least one planning target volume and an added non-anatomical region for its respective radiation therapy treatment.

The non-anatomical region may correspond to material configured to reduce or increase radiation emitted towards the planning target volume.

The non-anatomical region may have an electron density value or a mass density value corresponding to human flesh.

The attribute of the non-anatomical region may correspond to a thickness of the non-anatomical region.

The attribute of the non-anatomical region may correspond to a position of the non-anatomical region in relation to the planning target volume.

The attribute of the non-anatomical region may correspond to a position of the non-anatomical region compared to an organ of the patient.

Each medical image within the set of medical images may comprise an indication of whether its corresponding non-anatomical region is acceptable.

The instructions may further cause the processor to instruct a radiation therapy machine to adjust at least one of its attributes in accordance with the attribute of the non-anatomical region.

The instructions may further cause the processor to transmit the attribute of the non-anatomical region to a computing device to be displayed on a graphical user interface.

The instructions may further cause the processor to transmit a revised medical image that comprises the medical image not included in the set of medical images and a depiction of the non-anatomical region predicted by the machine-learning model.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Figure 1:
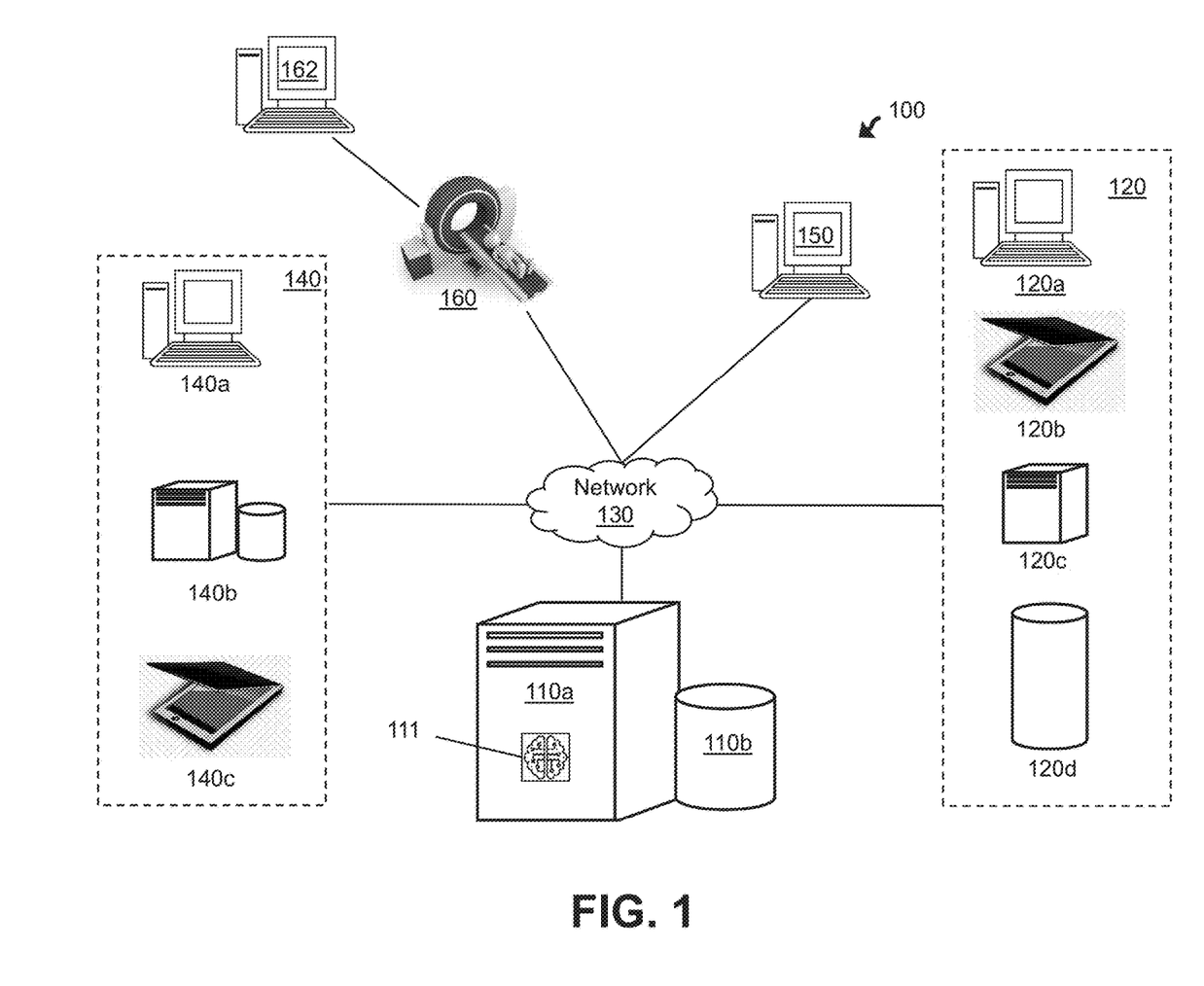
FIG. 1 illustrates components of an AI-based skinflash virtual bolus recommendation system, according to an embodiment.

FIG. 1 illustrates components of an AI-based skinflash virtual bolus recommendation system 100, according to an embodiment. The system 100 may include an analytics server 110a, system database 110b, machine-learning model 111, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160).

The above-mentioned components may be connected through a network 130. Examples of the network 130 may include but are not limited to, private or public LAN, WLAN, MAN, WAN, and the Internet. The network 130 may include wired and/or wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may train and execute the computer model 111 (including artificial intelligence and/or machine-learning models) to analyze medical images and predict attributes of a virtual bolus. More specifically, the computer model 111 may be a machine-learning model that is configured to retrieve patient data and treatment data, such as patient's medical images, physical attributes, treatment characteristics (e.g., tumor location and other information received via a treating physician), and other relevant data from the data sources 120. The computer model 111 is then configured to analyze the patient data, generate predictions and recommendations, and display the results on an electronic platform accessed by the end-user devices 140, the administrator computing device 150, and/or the medical device computer 162. In some embodiments, the computer model 111 is also configured to communicate with another computer model or a downstream model (e.g., a plan optimizer model) to generate and or revise a treatment plan for a patient. The analytics server 110a may transmit the predictions of the computer model 111 to the plan optimizer model where the plan optimizer model can optimize a treatment plan accordingly.

The electronic platform may display one or more recommendations predicted by the machine-learning model 111. The electronic platform may include a graphical user interface (GUI) displayed on each electronic data source 120, the end-user devices 140, the administrator computing device 150, and/or the medical device computer 162. An example of the electronic platform generated and hosted by the analytics server 110a may be a web-based application or a website configured to be displayed on different electronic devices, such as mobile devices, tablets, personal computers, and the like.

In a non-limiting example, a medical professional may access the electronic platform using an end-user device 140 to input a patient's treatment characteristics and attributes. For instance, a clinician may access the electronic platform to input the patient's medical images (e.g., CT scan), physical attributes (e.g., height, weight, or BMI), and/or diagnosis attributes (e.g., tumor location, medical images, PTV and/or OAR information, dose distribution thresholds) and/or any other information needed to perform the needed radiation therapy. The analytics server 110a may execute the computer model 111 to generate attributes of a virtual bolus for the patient and display the results on the electronic platform or transmit the results to a plan optimizer model (downstream software application).

Even though the computer model 111 is shown as being executed by the analytics server 110a, in other configurations, the computer model 111 may be stored in a third-party data repository and/or executed by a different server that may or may not be associated with the analytics server 110a. For instance, the analytics server 110a may transmit the patient data (e.g., medical images) to a second server (a third-party server not shown in FIG. 1), such that the second server can execute the computer model 111 model to generate the predictions.

The analytics server 110a may be any computing device comprising a processor and non-transitory machine-readable storage capable of executing the various tasks and processes described herein. The analytics server 110a may employ various processors such as central processing units (CPU) and graphics processing units (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110a may execute software applications configured to display the electronic platform (e.g., host a website), which may generate and serve various webpages to each electronic data source 120 and/or end-user devices 140. Different users may use the website to view and/or interact with the recommended (optimized) results to select field geometry attributes for treatment. The analytics server 110a may be configured to require user authentication based upon a set of user authorization credentials (e.g., username, password, biometrics, cryptographic certificate, and the like). The analytics server 110a may access the system database 110b configured to store user credentials, which the analytics server 110a may be configured to reference to determine whether a set of entered credentials (purportedly authenticating the user) match an appropriate set of credentials that identify and authenticate the user.

The analytics server 110a may generate and host webpages based upon a particular user's role within the system 100. In such implementations, the user's role may be defined by data fields and input fields in user records stored in the system database of the clinic server 110b. The analytics server 110a may authenticate the user and may identify the user's role by executing an access directory protocol (e.g., LDAP). The analytics server 110a may generate webpage content that is customized according to the user's role defined by the user record in the system database 110b.

The analytics server 110a may use the methods described herein to train and/or execute the model 111. The analytics server 110a may receive patient data (e.g., medical images, height, weight, diagnosis, age, equipment, etc.) from a user or retrieve such data from a data repository, analyze the data, and display the results on the electronic platform. The analytics server 110a may preprocess the patient data (e.g., automatically segment the medical image). For instance, in a non-limiting example, the analytics server 110a may query and retrieve medical images from the database 120d and combine the medical images with segment data received from a medical professional operating the medical professional device 120b and/or medical device 160 to perform preprocessing on the medical image (e.g., segment the medical image).

The analytics server 110a may execute the methods discussed herein to display the results of execution of the computer model 111 via the electronic platform on the administrator computing device 150, the medical professional device 120b, medical device computer 162, and/or the end-user devices 140.

The electronic data sources 120 may represent various electronic data sources that contain, retrieve, and/or input data associated with a patient's treatment plan including patient data and treatment data. For instance, the analytics server 110a may use the clinic computer 120a, medical professional device 120b, server 120c (associated with a physician and/or clinic), and database 120d (associated with the physician and/or the clinic) to retrieve or receive data associated with the patient's treatment plan. The analytics server 110a may use the data retrieved or received from the data sources 120 to train the computer model 111.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic server 140b, and a medical device professional 140c. Even though referred to herein as "end-user" devices, these devices may not always be operated by end-users. For instance, the clinic server 140b may not be directly used by an end-user. However, the results stored onto the clinic server 140b may be used to populate various GUIs accessed by an end-user via the medical professional device 140c.

The administrator computing device 150 may represent a computing device operated by a system administrator. The administrator computing device 150, along with the medical professional device 140c, medical professional device 120b, medical device computer 162, and the like, may be configured to display results from the execution of the machine-learning model 111. The administrator computing device 150 may also monitor the training of the machine-learning model 111 and input various thresholds and training parameters, as needed. For instance, the administrator computing device 150 may review feedback and/or facilitate training or retraining (calibration) of the machine-learning model 111 that is maintained by the analytics server 110a.

The medical device 160 may be a radiotherapy machine (e.g., a linear accelerator, particle accelerator (including circular accelerators), or a cobalt machine)) configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include stereo systems (e.g., two systems may be arranged orthogonally). The medical device 160 may also be in communication with a medical device computer 162 that is configured to display various GUIs discussed herein. For instance, the analytics server 110a may display the results predicted by the machine-learning model 111 onto the medical device computer 162.

In operation, a medical professional may access an application executing on the medical professional device 120b and input patient data (e.g., patient information, patient diagnosis, radiation therapy radiation requirements, and thresholds). The analytics server 110a then uses a patient identifier to query patient data (e.g., patient anatomy and/or medical images) from the electronic data sources 120. The analytics server 110a may then utilize the systems and methods described herein to generate a virtual bolus and/or recommend a treatment plan to be displayed on (and interacted with) one or more medical professionals.

The analytics server 110a may be in communication (real-time or near real-time) with the medical device computer 162, end-user device 140, and/or electronic data sources 120, such that a server/computer hosting the medical device 160 can adjust the medical device 160 based on the recommended (or selected) treatment attributes within the treatment plan. For instance, the radiotherapy machine may adjust the gantry, beam blocking device (e.g., multi-leaf collimator MLC), and couch based on field geometry attributes. The analytics server 110a may transmit instructions to the radiotherapy machines indicating any number or type of radiation parameters, beam angles, and/or treatment attributes to facilitate such adjustments.

Figure 2:
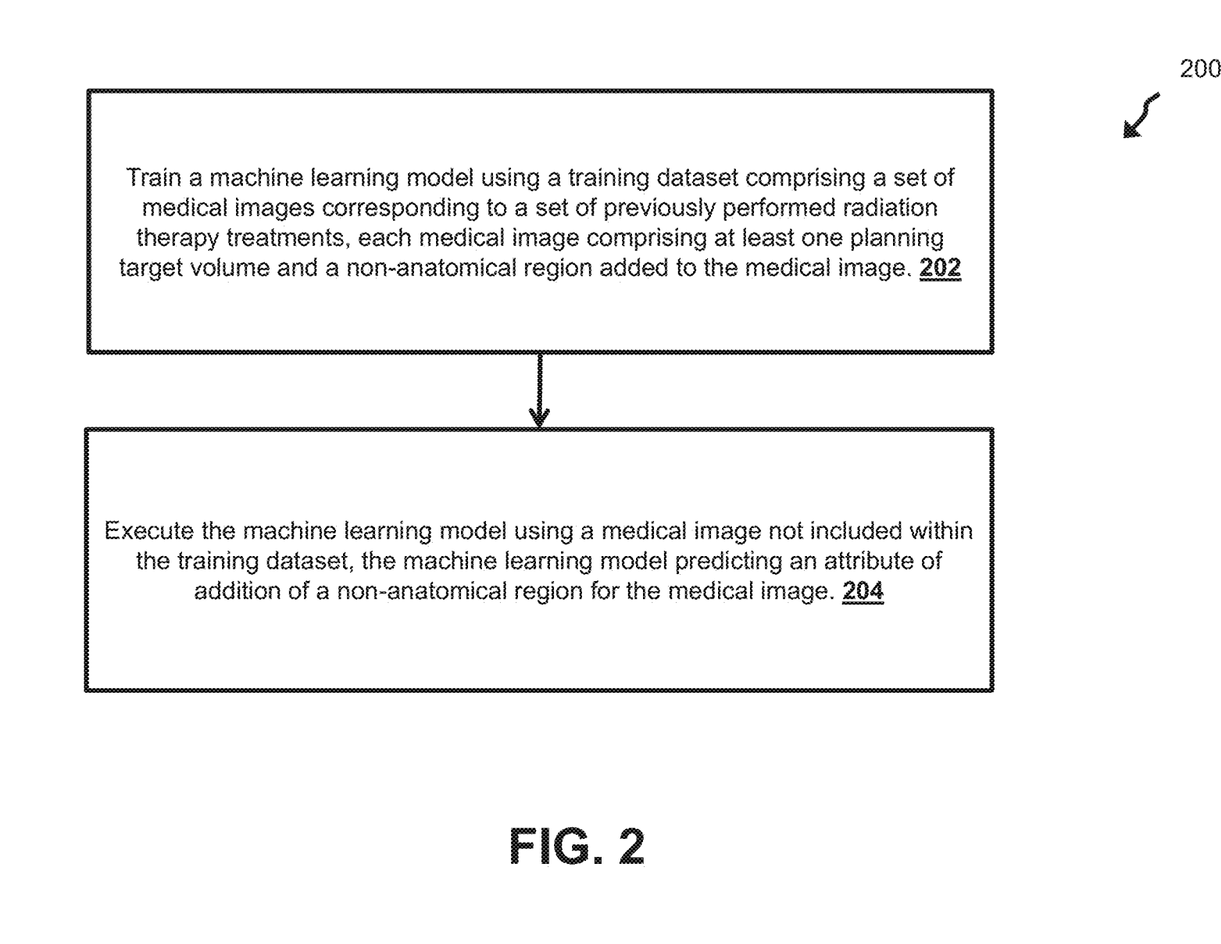
FIG. 2 illustrates a flow diagram of an AI-based skinflash virtual bolus recommendation system, according to an embodiment.

FIG. 2 illustrates a flow diagram of a radiotherapy treatment attribute recommendation system, according to an embodiment. The method 200 may be executed to train a machine-learning model, such that the trained model can be subsequently executed to monitor various parameters ingested by a plan optimizer model. The method 200 may include steps 202-204. However, other embodiments may include additional or alternative steps or may omit one or more steps altogether. The method 200 is described as being executed by a server, such as the analytics server described in FIG. 1. However, one or more steps of method 200 may be executed by any number of computing devices operating in the distributed computing system described in FIG. 1. For instance, one or more computing devices may locally perform part or all of the steps described in FIG. 2.

At step 202, the analytics server may train a machine-learning model using a training dataset comprising a set of medical images corresponding to a set of previously performed radiation therapy treatments, each medical image comprising at least one planning target volume, and a non-anatomical region added to the medical image.

In various embodiments, the machine-learning model uses one or more deep learning engines to perform automatic segmentation of images received. Although exemplified using deep convolutional neural networks, it should be understood that any alternative and/or additional deep learning model(s) may be used to implement deep learning engines. The deep learning engines include processing pathways that are trained during the training phase. Once trained, deep learning engines may be used (e.g., by a clinician) to determine attributes of a virtual bolus.

The analytics server may use a deep learning model trained on a clinically valid set of CT images, PTV segmentations, and virtual boluses to predict a new virtual bolus. The process may be analogous to the training of an organ segmentation model. However, the output of the model discussed herein is a virtual bolus structure.

One type of deep learning engine is a convolutional neural network (CNN). The CNN is a branch of neural networks and consists of a stack of layers each performing a specific operation, e.g., convolution, pooling, loss calculation, etc. Each intermediate layer receives the output of the previous layer as its input. The beginning layer is an input layer, which is directly connected to an input image and may have a number of neurons equal to the number of pixels in the input image. The next set of layers are convolutional layers that present the results of convolving a certain number of filters with the input data and perform as a feature extractor. The filters, commonly known as kernels, are of arbitrary sizes defined by designers. Each neuron responds only to a specific area of the previous layer, called the receptive field. The output of each convolution layer is considered as an activation map, which highlights the effect of applying a specific filter on the input. Convolutional layers may be followed by activation layers to apply non-linearity to the outputs of each layer. The next layer can be a pooling layer that helps to reduce the dimensionality of the convolution's output. In various implementations, high-level abstractions are extracted by fully connected layers. Alternatively, the analytics server may use deconvolution (also known as transpose convolution), normalization, dropout, concatenation to achieve results. The weights of neural connections and the kernels may be continuously optimized in the training phase.

In practice, training data may be user-generated through observations and experience to facilitate supervised learning. For example, training data may be extracted from past treatment plans developed for prior patients. In a non-limiting example, training data may include images of patients and their corresponding manually drawn virtual boluses. The training data may be pre-processed via any suitable data augmentation approach (e.g., rotation, flipping, translation, scaling, noise addition, cropping, any combination thereof, etc.) to produce a new dataset with modified properties to improve model generalization using ground truth.

The training dataset may include medical images associated with previously performed radiotherapy treatments. For instance, the training dataset may comprise data from previous patients that includes CT images, PTV data/attributes, body and virtual bolus structures, and the like (e.g., an image of the patient showing the tumor, the virtual bolus that was manually selected for the patient, the patient's tumor/PTV information, and the patient's body and disease information). Using the training methods discussed herein, the AI model may be trained to predict the virtual bolus based on the input of the CT and PTVs. For instance, the AI model may generate an overlay (or a mask) that includes the bolus (e.g., indicates various attributes of the bolus such as the position and thickness of the bolus). The model may then apply the overlay as an additional layer to the received CT image. The results predicted by the AI model (e.g., virtual PTV, which includes the actual PTV and the virtual bolus) may be used for plan optimization for the radiation therapy treatment (e.g., both IMRT and VMAT).

The training dataset may include labeled data. For instance, a medical professional (human reviewer) may analyze historical patient data and identify acceptable virtual boluses vs. unacceptable boluses. For instance, a doctor or a clinician may identify which medical images include correctly drawn virtual boluses. Using various training techniques, the machine-learning model may emulate the acceptable virtual boluses when generating the predicted virtual bolus for the new patient while avoiding attributes that lead to the reviewer marking some virtual boluses as unacceptable.

During training, the analytics server may iteratively produce new predicted results (recommendations) based on the training dataset (e.g., for each patient and their corresponding data within the dataset). If the predicted results do not match the real outcome, the analytics server continues the training unless and until the computer-generated recommendation satisfies one or more accuracy thresholds and is within acceptable ranges. For instance, the analytics server may segment the training dataset into three groups (i.e., training, validation, and test). The analytics server may train the AI model based on the first group (training). The analytics server may then execute the (at least partially) trained AI model to predict results for the second group of data (validation). The analytics server then verifies whether the prediction is correct. Using the above-described method, the analytics server may evaluate whether the AI model is properly trained. The analytics server may continuously train and improve the model using this method. The analytics server may then gauge the AI model's accuracy (e.g., area under the curve, precision, and recall) using the remaining data points within the training dataset (test).

At step 204, the analytics server may execute the machine-learning model using a medical image not included within the training dataset, the machine-learning model predicting an attribute of addition of a non-anatomical region for the medical image not included in the training dataset. The analytics server may execute the trained machine-learning model using the patient data. As a result, the analytics server may identify a virtual bolus based on patient data. For instance, the analytics server may predict one or more attributes of the virtual bolus, such as thickness, type, length, and placement for the virtual bolus. In some configurations, the analytics server may identify placement of the virtual bolus in relation to an anatomical region of the patient (e.g., compared to the PTV). The predicted results can be displayed on a computing device of the user (e.g., the clinician) in form of a masked image or numerical values indicating attributes of the virtual bolus. For instance, the analytics server may display a GUI indicating that the "skinflash" tool is on and the analytics server has identified a virtual bolus for the patient. The analytics server may then display an image of the virtual bolus and an overlay of the patient's medical image.

Figure 3:
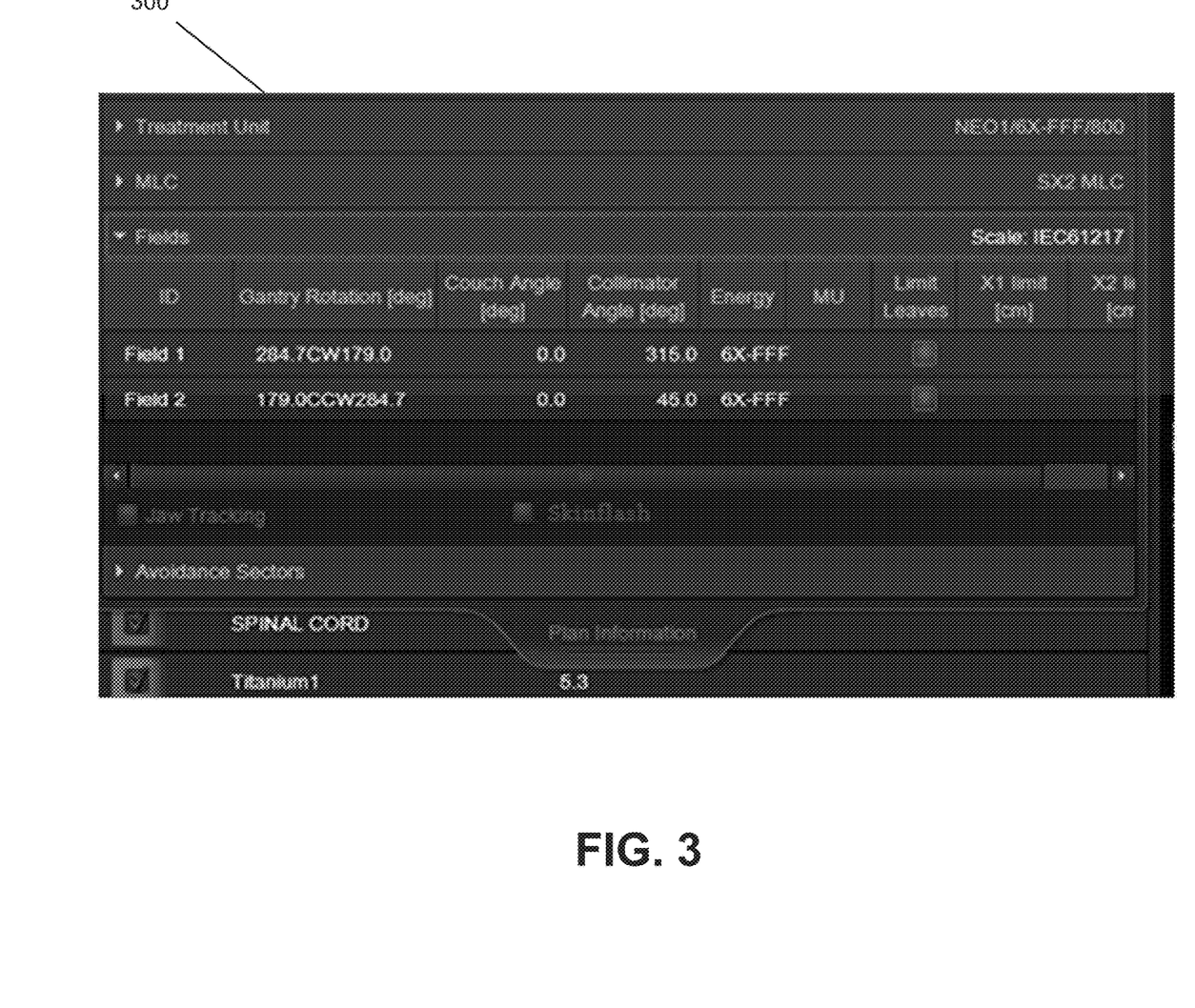
FIG. 3 illustrates a graphical user interface displayed by the AI-based skinflash virtual bolus recommendation system, according to an embodiment.

In a non-limiting example, as depicted in FIG. 3, the analytics server may display the GUI 300 that includes a graphical representation of the virtual bolus. Skinflash, as used herein, may refer to MLC openings adjusted to better account for breathing motion and other changes in the body outline of a patient being treated under photon breast treatment plans. To create skinflash MLC openings, the analytics server may generate contours of a virtual bolus (e.g., with preferred density (0 or 100 HU)) and may extend the PTV and the patient's body on top of the virtual bolus.

Additionally or alternatively, the virtual bolus information may be used to generate a treatment plan for the patient. For instance, a plan optimizer (e.g., a computer model configured to iteratively optimize various attributes of a treatment plan) may optimize the patient's treatment plan using the new structure set (e.g., virtual bolus). Therefore, the predictions generated by the analytics server (e.g., via the machine-learning models discussed herein) can be fed into a downstream application. The virtual bolus generated by the analytics server may be considered as a helping structure to guide the optimization of the patient's treatment plan. As a result, no clinician is required to identify (e.g., draw) a virtual bolus for the patient's treatment. For instance, in the final step of optimizing the patient's planning, the user may apply the treatment plan to the original structure set and re-calculate the final dose needed for the patient.

Using the methods and systems discussed herein, the analytics server can generate/predict a virtual bolus. Additionally, the predicted virtual bolus can be used for treatment planning purposes. However, in some configurations, the virtual bolus may only be displayed and not used for down-stream software/applications.

The analytics server may display a GUI indicating that the skinflash tool is using a virtual bolus to optimize the patient's treatment, as depicted in FIG. 3. The GUI 300 indicates that the analytics server is using an automatic skinflash tool to optimize MLC openings. The GUI 300 may also indicate radiotherapy machine attributes, such as gantry rotation values, couch angle, collimator angle, and the like.

The analytics server may apply an automation step to modify the Hounsfield units (HU) value of the bolus and to combine those values with the PTV before optimization. As a result, the output may be a new structure: PTV+PTV extension on top of the bolus. The analytics server may use this technique as a target in the optimization process. In some configurations, the analytics server may automatically switch to the original PTV (e.g., analyze the data associated with the original PTV) for the final dose calculation.

Figure 4:
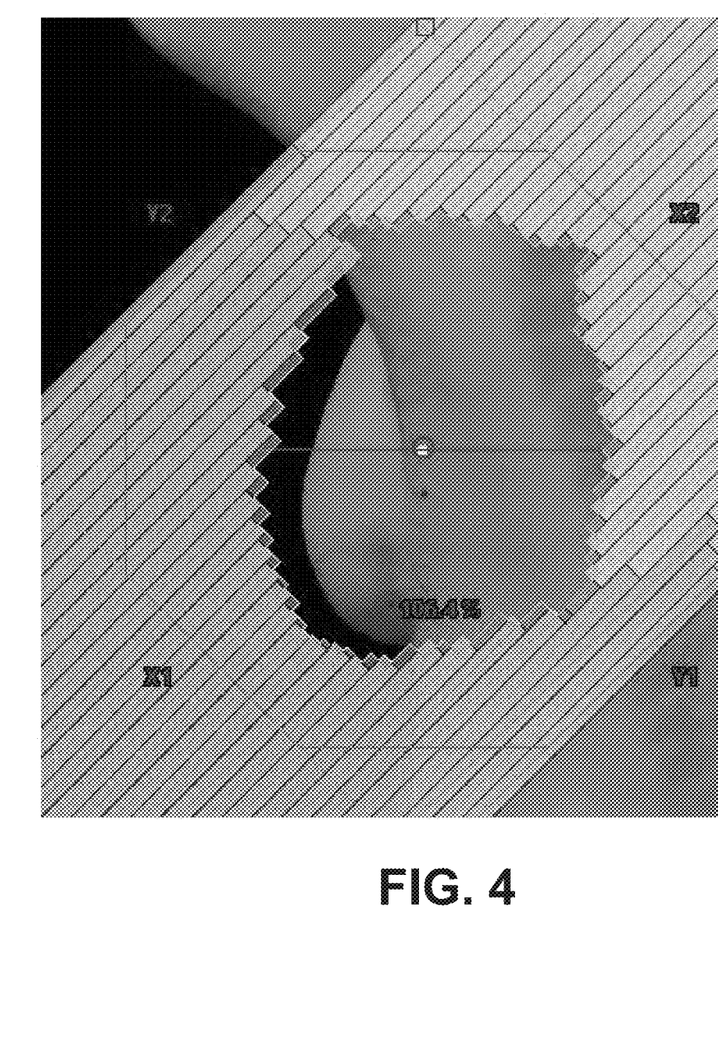
FIG. 4 illustrates a multi-leaf collimator opening, according to an embodiment.

Using the optimization and dose calculation methods discussed herein, the analytics server may also create a leaf sequence that leaves a margin outside the PTV (as depicted in FIG. 4). In this way, the analytics server can ensure that the PTV will receive the prescribed radiation dose even in the presence of patient movement (e.g., breathing movement). FIG. 4 depicts the final leaf opening from a single beams-eye-view of a treatment field. The depicted openings may leave a margin outside the body ensuring that radiation will not miss the PTV in the case of chest movement. In some configurations, the analytics server may automatically instruct a radiotherapy machine to adjust its MLC opening. Therefore, the analytics server may provide a fully automated system in which the patient's data is analyzed and radiotherapy adjustments are implemented without user intervention or input.

In some configurations, the IMRT planning could optimize a treatment plan using the real PTV structure (and other attributes necessary to generate a treatment plan) and control the leaf opening based on the projection of the virtual bolus predicted by the AI model (e.g., adjust the opening for each beam based on the each respective field's beam). The methods and systems discussed herein are not limited to IMRT. Therefore, the virtual bolus prediction can be used for VMAT conformal arc, tangential fields, and the like.

Figure 5:
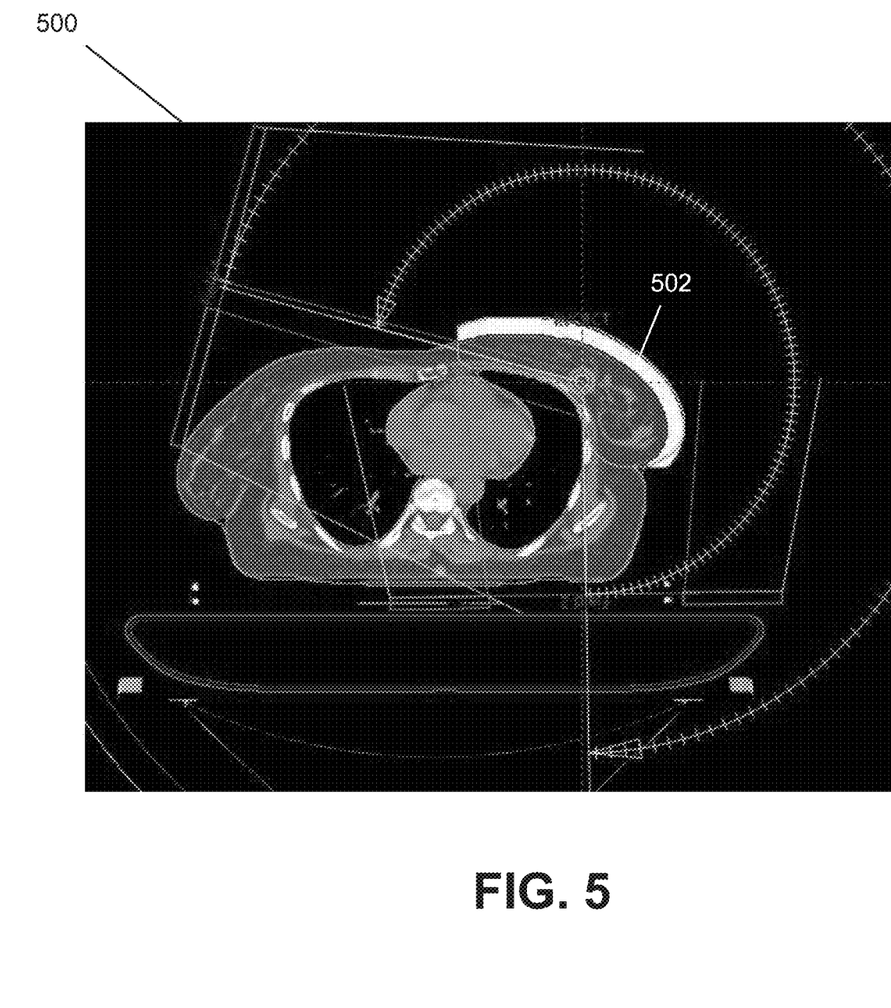
FIG. 5 illustrates a graphical user interface displayed by the AI-based skinflash virtual bolus recommendation system, according to an embodiment.

Additionally or alternatively, the analytics server may display a representation of the virtual bolus. For instance, as depicted in FIG. 5, the analytics server may display the GUI 500 that depicts a medical image of the patient that includes a virtual bolus mask 502 that is generated using the methods and systems described herein. The analytics server may overlay the virtual bolus mask 502 as an additional layer to the medical image depicted on the GUI 500.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate the transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   executing, by a processor, a machine-learning model using a medical image not used to train the machine-learning model to predict an attribute of a non-anatomical region for the medical image, the non-anatomical region being located on an outer surface of a patient, wherein the machine-learning model has been trained using a set of medical images corresponding to a set of previously performed radiation therapy treatments, each medical image comprising at least one planning target volume and an added non-anatomical region for its respective radiation therapy treatment.

2. The method of claim 1, wherein the non-anatomical region corresponds to material configured to reduce or increase radiation emitted towards the planning target volume.

3. The method of claim 1, wherein the non-anatomical region has an electron density value or a mass density value corresponding to human flesh.

4. The method of claim 1, wherein the attribute of the non-anatomical region corresponds to a thickness of the non-anatomical region.

5. The method of claim 1, wherein the attribute of the non-anatomical region corresponds to a position of the non-anatomical region in relation to the planning target volume.

6. The method of claim 1, wherein the attribute of the non-anatomical region corresponds to a position of the non-anatomical region compared to an organ of the patient.

7. The method of claim 1, wherein each medical image within the set of medical images comprises an indication of whether its corresponding non-anatomical region is acceptable.

8. The method of claim 1, further comprising:
instructing, by the processor, a radiation therapy machine to adjust at least one of its attributes in accordance with the attribute of the non-anatomical region.

9. The method of claim 1, further comprising:
transmitting, by the processor, the attribute of the non-anatomical region to a computing device to be displayed on a graphical user interface.

10. The method of claim 1, further comprising:
transmitting, by the processor, a revised medical image that comprises the medical image not used for training the machine-learning model and a depiction of the non-anatomical region predicted by the machine-learning model.

11. A system comprising:
a server comprising a processor and a non-transitory computer-readable medium containing instructions that when executed by the processor causes the processor to perform operations comprising:
executing a machine-learning model using a medical image not used to train the machine-learning model to predict an attribute of a non-anatomical region for the medical image, the non-anatomical region being located on an outer surface of a patient, wherein the machine-learning model has been trained using a set of medical images corresponding to a set of previously performed radiation therapy treatments, each medical image comprising at least one planning target volume and an added non-anatomical region for its respective radiation therapy treatment.

12. The system of claim 11, wherein the non-anatomical region corresponds to material configured to reduce or increase radiation emitted towards the planning target volume.

13. The system of claim 11, wherein the non-anatomical region has an electron density value or a mass density value corresponding to human flesh.

14. The system of claim 11, wherein the attribute of the non-anatomical region corresponds to a thickness of the non-anatomical region.

15. The system of claim 11, wherein the attribute of the non-anatomical region corresponds to a position of the non-anatomical region in relation to the planning target volume.

16. The system of claim 11, wherein the attribute of the non-anatomical region corresponds to a position of the non-anatomical region compared to an organ of the patient.

17. The system of claim 11, wherein each medical image within the set of medical images comprises an indication of whether its corresponding non-anatomical region is acceptable.

18. The system of claim 11, wherein the instructions further cause the processor to instruct a radiation therapy machine to adjust at least one of its attributes in accordance with the attribute of the non-anatomical region.

19. The system of claim 11, wherein the instructions further cause the processor to transmit the attribute of the non-anatomical region to a computing device to be displayed on a graphical user interface.

20. The system of claim 11, wherein the instructions further cause the processor to transmit a revised medical image that comprises the medical not used for training the machine-learning model and a depiction of the non-anatomical region predicted by the machine-learning model.

* * * * *